United States Patent
Petcavich (10) Patent No.: US 10,760,053 B2
(45) Date of Patent: Sep. 1, 2020

(54) METHOD OF MANUFACTURING OR DIFFERENTIATING MAMMALIAN PLURIPOTENT STEM CELLS OR PROGENITOR CELLS USING A HOLLOW FIBER BIOREACTOR

(71) Applicant: StemoniX Inc., Eden Prairie, MN (US)

(72) Inventor: Robert John Petcavich, The Woodlands, TX (US)

(73) Assignee: StemoniX Inc., Eden Prairie, MN (US)

( * ) Notice: Subject to any disclaimer, the term of this patent is extended or adjusted under 35 U.S.C. 154(b) by 99 days.

(21) Appl. No.: 15/293,563

(22) Filed: Oct. 14, 2016

(65) Prior Publication Data

US 2017/0107488 A1   Apr. 20, 2017

Related U.S. Application Data

(60) Provisional application No. 62/347,208, filed on Jun. 8, 2016, provisional application No. 62/241,977, filed on Oct. 15, 2015.

(51) Int. Cl.
*C12N 5/0797* (2010.01)
*C12M 1/12* (2006.01)

(52) U.S. Cl.
CPC ........... *C12N 5/0623* (2013.01); *C12M 25/10* (2013.01); *C12N 2533/30* (2013.01); *C12N 2533/78* (2013.01)

(58) Field of Classification Search
CPC .............. C12N 5/0623; C12N 2533/30; C12N 2533/78; C12M 25/10
See application file for complete search history.

(56) References Cited

U.S. PATENT DOCUMENTS

| | | | |
|---|---|---|---|
| 5,981,268 A | 11/1999 | Kovacs et al. | |
| 6,565,813 B1 | 5/2003 | Garyantes | |
| 2002/0049160 A1 | 4/2002 | Huang et al. | |
| 2004/0067546 A1 | 4/2004 | Leng et al. | |
| 2005/0169962 A1 | 8/2005 | Bhatia et al. | |
| 2007/0017530 A1 | 1/2007 | Syed et al. | |
| 2007/0122392 A1 | 5/2007 | Gerecht-Nir et al. | |
| 2007/0280987 A1 | 12/2007 | Helmus et al. | |
| 2008/0009517 A1 | 1/2008 | Gupta et al. | |
| 2008/0193536 A1 | 8/2008 | Khademhosseini et al. | |
| 2010/0055733 A1 | 3/2010 | Lutolf et al. | |
| 2010/0120626 A1 | 5/2010 | Ross et al. | |
| 2010/0317103 A1* | 12/2010 | Cho et al. .................... | 435/366 |
| 2011/0306041 A1 | 12/2011 | Viovy et al. | |
| 2012/0053084 A1 | 3/2012 | Gerber et al. | |
| 2012/0149781 A1 | 6/2012 | Lee et al. | |
| 2012/0308531 A1 | 12/2012 | Pinxteren et al. | |
| 2013/0029421 A1 | 1/2013 | Komvopoulos et al. | |
| 2013/0034904 A1 | 2/2013 | Fan et al. | |
| 2013/0171116 A1 | 7/2013 | Shoham et al. | |
| 2013/0203086 A1 | 8/2013 | Achyuta et al. | |
| 2013/0217113 A1 | 8/2013 | Srinivasan et al. | |
| 2014/0142370 A1 | 5/2014 | Wong et al. | |
| 2014/0287506 A1* | 9/2014 | Sanyal et al. ......... | C12N 5/0602 435/396 |
| 2015/0301028 A1 | 10/2015 | Eggan et al. | |
| 2016/0059203 A1 | 3/2016 | Petcavich | |
| 2017/0002324 A1 | 1/2017 | Petcavich | |
| 2017/0166857 A1 | 6/2017 | Petcavich | |
| 2018/0113118 A1 | 4/2018 | Petcavich | |
| 2018/0291336 A1 | 10/2018 | Petcavich | |
| 2019/0161717 A1 | 5/2019 | Petcavich | |
| 2019/0177691 A1 | 6/2019 | Petcavich | |

FOREIGN PATENT DOCUMENTS

| | | |
|---|---|---|
| CN | 102156158 A | 8/2011 |
| DE | 102014003465 A1 | 9/2015 |
| JP | 2003503715 A | 1/2003 |
| JP | 2005505747 A | 2/2005 |
| JP | 2007516699 A | 6/2007 |
| JP | 2008199962 A | 9/2008 |
| JP | 2013135685 | 7/2013 |
| JP | 2014519825 A | 8/2014 |
| JP | 2017532061 A | 11/2017 |

(Continued)

OTHER PUBLICATIONS

US 10,562,004 B2, 02/2020, Petcavich (withdrawn)
Garcia-Parra et al., "Modeling neural differentiation on micropatterned substrates coated with neural matrix components", Frontiers in Cellular Neuroscience, Mar. 14, 2012, vol. 6, article 10, pp. 1-12. (Year: 2012).*
Hazeltine L.B. et al., "Engineering the human pluripotent stem cell microenvironment to direct cell fate", Biotechnol. Adv., Nov. 15, 2013; vol. 31, No. 7, pp. 1-38. (Year: 2013).*
"International Application Serial No. PCT US2016 057172, International Preliminary Report on Patentability dated Apr. 26, 2018", 7 pgs.
"International Application Serial No. PCT/US2016/057172, International Search Report dated Jan. 17, 2017", 5 pgs.

(Continued)

*Primary Examiner* — Satyendra K Singh
(74) *Attorney, Agent, or Firm* — Schwegman Lundberg & Woessner, P.A.

(57) ABSTRACT

The present disclosure provides a method of manufacturing and differentiating mammalian stem cells, and in one embodiment human induced pluripotent stem cells (iPSc), e.g., manufacturing neuron progenitors, e.g., derived from iPSC, on a large scale by the use of an automated hollow fiber reactor system. In one embodiment, human iPSc that can be differentiated into cardiomyocytes or neuron progenitors are provided. The method comprises seeding a hollow fiber reactor with stem cells such as iPSc, or differentiated iPSc, growing and expanding the seeded cells using appropriate growth factors and nutrients, and harvesting the cells after expansion from the hollow fiber reactor walls, e.g., with the use of an enzyme. The method can produce billions of cells per week from seeding the reactor with a minimum number of starting stem cells or neuron progenitor cells.

10 Claims, 3 Drawing Sheets

(56) References Cited

FOREIGN PATENT DOCUMENTS

| JP | 2018536424 A | 12/2018 |
|---|---|---|
| JP | 2018537073 A | 12/2018 |
| SG | 2011088213 | 7/2011 |
| SG | 2014063194 | 5/2014 |
| WO | WO-2011/088213 A1 | 7/2011 |
| WO | WO-2012168295 A1 | 12/2012 |
| WO | WO-2014063194 A1 | 5/2014 |
| WO | WO-2014110559 A1 | 7/2014 |
| WO | 2014145975 | 9/2014 |
| WO | WO-2014144219 A1 | 9/2014 |
| WO | 2015/069943 | 5/2015 |
| WO | WO-2016033501 A1 | 3/2016 |
| WO | WO-2016090486 A1 | 6/2016 |
| WO | 2017066663 | 4/2017 |
| WO | WO-2017100705 A1 | 6/2017 |
| WO | WO-2018026925 A1 | 2/2018 |
| WO | WO-2018026929 A1 | 2/2018 |
| WO | WO-2018075890 A1 | 4/2018 |

OTHER PUBLICATIONS

"International Application Serial No. PCT/US2016/057172, International Written Opinion dated Jan. 17, 2017", 5 pgs.
"U.S. Appl. No. 14/839,170, Advisory Action dated Jun. 5, 2018", 4 pgs.
"U.S. Appl. No. 14/839,170, Final Office Action dated Jan. 30, 2019", 19 pgs.
"U.S. Appl. No. 14/839,170, Final Office Action dated Mar. 12, 2018", 12 pgs.
"U.S. Appl. No. 14/839,170, Non Final Office Action dated Feb. 9, 2017", 8 pgs.
"U.S. Appl. No. 14/839,170, Non Final Office Action dated Sep. 7, 2018", 19 pgs.
"U.S. Appl. No. 14/839,170, Response filed Jan. 7, 2019 to Non Final Office Action dated Sep. 7, 2018", 10 pgs.
"U.S. Appl. No. 14/839,170, Response filed Jan. 11, 2017 to Restriction Requirement dated Nov. 18, 2016", 6 pgs.
"U.S. Appl. No. 14/839,170, Response filed May 9, 2017 to Non Final Office Action dated Feb. 9, 2017", 7 pgs.
"U.S. Appl. No. 14/839,170, Response filed May 14, 2018 to Final Office Action dated Mar. 12, 2018", 7 pgs.
"U.S. Appl. No. 14/839,170, Response filed Jul. 12, 2018 to Final Office Action dated Mar. 12, 2018", 7 pgs.
"U.S. Appl. No. 14/839,170, Restriction Requirement dated Nov. 18, 2016", 6 pgs.
"U.S. Appl. No. 15/199,419, Advisory Action dated Jul. 20, 2018", 5 pgs.
"U.S. Appl. No. 15/199,419, Final Office Action dated Apr. 16, 2018", 19 pgs.
"U.S. Appl. No. 15/199,419, Non Final Office Action dated Jan. 25, 2019", 25 pgs.
"U.S. Appl. No. 15/199,419, Non Final Office Action dated Nov. 8, 2017", 21 pgs.
"U.S. Appl. No. 15/199,419, Response filed Feb. 8, 2017 to Non Final Office Action dated Nov. 8, 2017", 14 pgs.
"U.S. Appl. No. 15/199,419, Response filed Aug. 16, 2018 to Final Office Action dated Apr. 16, 2018", 8 pgs.
"U.S. Appl. No. 15/199,419, Response filed Aug. 29, 2017 to Restriction Requirement dated Jun. 23, 2017", 6 pgs.
"U.S. Appl. No. 15/199,419, Response filed Jun. 19, 2018 to Final Office Action dated Apr. 16, 2018", 9 pgs.
"U.S. Appl. No. 15/199,419, Restriction Requirement dated Jun. 23, 2017", 10 pgs.
"U.S. Appl. No. 15/374,961, Non Final Office Action dated Nov. 30, 2018", 15 pgs.
"U.S. Appl. No. 15/374,961, Response filed Oct. 2, 2018 to Restriction Requirement dated Aug. 2, 2018", 6 pgs.
"U.S. Appl. No. 15/374,961, Restriction Requirement dated Aug. 2, 2018", 7 pgs.
"U.S. Appl. No. 15/789,335, Restriction Requirement dated Feb. 7, 2019", 8 pgs.
"European Application Serial No. 15762878.5, Communication Pursuant to Article 94(3) EPC dated Jan. 4, 2018", 5 pgs.
"European Application Serial No. 15762878.5, Communication Pursuant to Article 94(3) EPC dated Nov. 20, 2018", 4 pgs.
"European Application Serial No. 15762878.5, Response filed Jul. 16, 2018 to Communication Pursuant to Article 94(3) EPC dated Jan. 4, 2018", 34 pgs.
"European Application Serial No. 15762878.5, Response filed Oct. 16, 2017 to Communication pursuant to Rules 161(1) and 162 EPC dated Apr. 4, 2017", 9 pgs.
"European Application Serial No. 16829018.7, Response filed Feb. 5, 2019 to Communication Pursuant to Rules 161(1) and 162 EPC dated Jul. 26, 2019", 8 pgs.
"International Application Serial No. PCT/US15/47494, International Search Report dated Nov. 6, 2015", 4 pgs.
"International Application Serial No. PCT/US15/47494, Written Opinion dated Nov. 6, 2015", 6 pgs.
"International Application Serial No. PCT/US2015/047494, International Preliminary Report on Patentability dated Mar. 9, 2017", 8 pgs.
"International Application Serial No. PCT/US2016/066014, International Preliminary Report on Patentability dated Jun. 21, 2018", 8 pgs.
"International Application Serial No. PCT/US2016/066014, International Search Report dated Apr. 5, 2017", 5 pgs.
"International Application Serial No. PCT/US2016/066014, Written Opinion dated Apr. 5, 2017", 9 pgs.
"International Application Serial No. PCT/US2017/045114, International Search Report dated Oct. 23, 2017", 5 pgs.
"International Application Serial No. PCT/US2017/045114, Written Opinion dated Oct. 23, 2017", 7 pgs.
"International Application Serial No. PCT/US2017/045119, International Search Report dated Oct. 27, 2017", 3 pgs.
"International Application Serial No. PCT/US2017/045119, Written Opinion dated Oct. 27, 2017", 6 pgs.
"International Application Serial No. PCT/US2017/057591, International Search Report dated Jan. 30, 2018", 6 pgs.
"International Application Serial No. PCT/US2017/057591, Written Opinion dated Jan. 30, 2018", 5 pgs.
"Japanese Application Serial No. 2017-530976, Office Action dated Jul. 30, 2018", w/ English translation, 7 pgs.
"Japanese Application Serial No. 2017-530976, Response filed Oct. 3, 2018 to Office Action dated Jul. 3, 2018", w/ English Claims, 12 pgs.
"Singaporean Application Serial No. 11201701540P, Response filed Aug. 24, 2017 to Request Combined Search and Examination dated Feb. 27, 2017", 9 pgs.
"Singaporean Application Serial No. 11201701540P, Written Opinion dated Nov. 7, 2018", 6 pgs.
"Singaporean Application Serial No. 11201701540P, Written Opinion dated Dec. 28, 2017", 7 pgs.
Ali, Khademhosseini, et al., "Micromolding of photoelectrically hyaluronic acid for cell encapsulation and entrapment", Journal of Biomedical Materials Research Part A, vol. 79A, No. 3, (Jan. 1, 2006), 522-532.
Alireza, Dolatshahi Pirouz, et al., "A combinatorial cell-laden gel microarray for inducing osteogenic differentiation of human mesenchymal stem cells", Scientific Reports, vol. 4, (Jan. 29, 2014), 2 pgs.
Anke, Tukker, "Is the time right for in vitro neurotoxicity testing using human iPSC-derived neurons?", Alternatives to Animal Experimentation: ALTEX, (Jan. 1, 2016).
Blau, Axel, "Cell adhesion promotion strategies for signal transduction", Current Opinion in Colloid & Interface Science 18, (2013), 481-492.
Booth, Ross, et al., "Characterization of microfluidic in vitro model of the blood-brain barrier (μBBB)", Lab on Chip Royal Society of Chemistry vol. 12, No. 10, (Jan. 1, 2012), 1784-1792.

(56) References Cited

OTHER PUBLICATIONS

Braam, et al., "Inhibition of ROCK improves survival of human embryonic stem cell-derived cardiomyocytes after dissociation", Annals of the New York Academy of Science,1188, (2010), 52-57 pgs.

Brewer, G J, et al., "Gold-Coated Microelectrode Array With Thiol Linked Self-Assembled Monolayers for Engineering Neuronal Cultures,", IEEE Transactions on Biomedical Engineering vol. 51, No. 1, (Jan. 1, 2004), 158-165.

Chen, J, et al., "Ch. 18: In vitro and in vivo assays for the discovery of analgesic drugs targetting TRP channels", TRP Channels, (Dec. 31, 2011).

Claverol-Tinture, E, et al., "Multi electrode arrays with elastomeric microstructured overlays for extracellular recordings from patterned neurons", Communication; Journal of Neural Engineering, Institute of Physics Publishing, Bristol, GB, vol. 2, No. 2 (Jun. 1, 2005), L1-L7.

Dib-Hajj, Sulayman D, et al., "Human pain in a dish: Native DRG neurons and differentiated pluripotent stem cells", IASP Pain 155, (Sep. 2014), 1681-1682.

Dolatshahi-Pirouz, Alireza, et al., "A combinatorial cell-laden gel microarray for inducing osteogenic differentiation of human mesenchymal stem cells", Scientific Reports, (Jan. 29, 2014), 1-9.

Fernandes, et al., "High-throughput cellular microarray platforms: applications in drug discovery, toxicology and stem cell research", Trends in Biotechnology, 27(6), (2009), 342-349.

Geyer, et al., "Superhydrophobic-Superhydrophilic Micropatterning: Towards Genome on a Chip Cell Microarrays", Angewandte Chemie, 50, (2011), 8424-27.

Geyer, Florian L, et al., "Superhydrophobic-Superhydrophilic Micropatterning: Towards Genome-on-a-Chip Cell Microarrays", Angewandte Chemie International Edition, vol. 50, Issue 36, (2011), pp. 8424-8427.

Gi, Seok Jeong, et al., "Networked neural spheroid by neuro-bundle mimicking nervous system created by topology effect", Molecular Brain, Biomed Central Ltd, London UK, vol, 8, No. 1, (Mar. 22, 2015), 17.

Hayder, Amin, et al., "Electrical Responses and Spontaneous Activity of Human iPS-Derived Neuronal Networks Characterized for 3-month Culture with 4096-Electrode Arrays", Frontiers in Neuroscience, vol. 10, (Mar. 30, 2016).

Heller, D, et al., "Patterned networks of mouse hippocampal neurons on peptide-coated gold surfaces", Biomaterials vol. 26, No. 8, (Mar. 1, 2005), 883-889.

Jack, Wang D, et al., "Organization of Endothelial Cells, Pericytes, and Astrocytes into 3D Microfluidic in Vitro Model of the Blood-Brain Barrier", Molecular Pharmaceutics, vol. 13 No. 3, (Mar. 7, 2016), 895-906.

Jacquelyn, Brown, et al., "Recreating blood-brain barrier physiology and structure on chip novel neurovascular microlluidic bioreactor", Biomicrofluidics, vol. 9 No. 5, (Sep. 1, 2015), 16 pgs.

Kathe, Stanness, et al., "Morphological and functinoal characterization of an in vitro blood-brain barrier model", Brain Research vol. 771 No. 2, (Oct. 1, 1997), 329-342.

Kim, Yong Hee, et al., "In vitro extracellular recording and stimulation performance", Journal of Neural Engineering, (Nov. 24, 2015), 10 pgs.

Krinke, Dana, et al., "A microelectrode-based sensor for label-free in vitro detection of ischemic effects on cardiomyocytes", Biosensors and Bioelectronics vol. 24, No. 15, (May 15, 2009), 2798-2803.

Luca, Cucullo, et al., "Development of a Humanized In Vitro Blood?Brain Barrier Model to Screen for Brain Penetration of Antiepileptic Drugs", Epilepsia, vol. 48 No. 3, New York US, (Mar. 1, 2007), 505-516.

Maher, et al., "The neurochip: a new multielectrode device for stimulating and recording from cultured neurons", Journal of Neuroscience Methods vol. 87 No. 1, (Feb. 1, 1999), 45-56.

Maher, M, et al., "A microstructure for interfacing with neurons: the neurochip", Engineering in Medicine and Biology Society,1998. Proceedings of The20th Annual International Conference of the IEEE, IEEE—Piscataway, NJ, US, vol. 4, (Oct. 29, 1998), 1698-1702.

Mohammad, A Kaisar, et al., "New experimental models of the blood-brain barrier for CNS drug discovery", Expert Opinion on Drug Discovery, (Nov. 7, 2016), 89-103.

Mordwinkin, et al., "A Review of Human Pluripotent Stem Cell-Derived Cardiomyocytes for High-Throughput Drug Discovery, Cardiotoxicity Screening and Publication Standards", Journal of Cardiovascular Translational Research, 6(1), (2013), 22-30.

Musick, Katherine, et al., "Three-dimensional micro-electrode array for recording dissociated neuronal cultures", Lab Chip., (Feb. 9, 2010), 18 pgs.

Naik, Pooja, et al., "In Vitro Blood—Brain Barrier Models: Current and Perspective Technologies", J Pharm Sci., (Apr. 2012), 30 pgs.

Nichol, J W, et al., "Cell-laden microengineered gelatin methacrylate hydrogels", Biomaterials Elsevier Science Publishers BV Barking GB, vol. 31, No. 21, (Jan. 7, 2010), 5536-5544.

Nichol, Jason W., et al., "Cell-laden microengineered gelatin methacrylate hydrogels", National Institutes of Health, (Jul. 31, 2010), 1-20.

Panke, O, et al., "A cell-based impedance assay for monitoring transient receptor potential (TRP) ion channel activity", Biosensors and Bioelectronics vol, 26 No. 5, (Jan. 15, 2011), 2376-2382.

Paradis, Alexandre, et al., "Optimizationofaninvitrohumanblood—brain barrier model:", MethodsX 3, (2016), 25-34.

Peppas, Nicholas A., et al., "Hydrogels in Biology and Medicine: From Molecular Principles ot Bionanotechnology", Advanced Materials, (2006), 1345-1360.

Salisbury, David, "Blood-brain barrier on a chip sheds new light on "silent killer"", New.Vanderbilt EDU, [Online] Retrieved frmo the internet: <https://news.vanderbilt.edu/2016/06/blood-brain-barrier-on-a-chip-sheds-new-light-on-silent-killer/>, (Dec. 6, 2016), 6 pgs.

Wong, et al., "Advancing Microarray Assembly with Acoustic Dispensing Technology", Analytical Chemistry, 81, (Jan. 1, 2009), 509-514 pgs.

Yuan, Y., et al., "Contact angle and wetting properties", In: Surface Scientific Techniques. Chapter 1. Copyright 2013 Springer-Verlag, Berlin/Heidelberg. Eds.: Bracco, G & Hoist, B., 3-34.

"U.S. Appl. No. 14/839,170, Notice of Allowance dated Jun. 10, 2019", 10 pgs.

"U.S. Appl. No. 14/839,170, Response filed Apr. 30, 2019 to Final Office Action dated Jan. 30, 2019", 10 pgs.

"U.S. Appl. No. 15/199,419, Final Office Action dated May 30, 2019", 25 pgs.

"U.S. Appl. No. 15/199,419, Response filed Apr. 23, 2019 to Non Final Office Action dated Jan. 25, 2019", 10 pgs.

"U.S. Appl. No. 15/374,961, Final Office Action dated Jun. 13, 2019", 17 pgs.

"U.S. Appl. No. 15/374,961, Response filed Feb. 28, 2019 to Non Final Office Action dated Nov. 30, 2018", 7 pgs.

"U.S. Appl. No. 15/789,335, Non Final Office Action dated Jul. 26, 2019", 21 pgs.

"U.S. Appl. No. 15/789,335, Response filed Apr. 8, 2019 to Restriction Requirement dated Feb. 7, 2019", 5 pgs.

"European Application Serial No. 16829018.7, Communication Pursuant to Article 94(3) EPC dated May 28, 2019", 6 pgs.

"International Application Serial No. PCT/US2017/045114, International Preliminary Report on Patentability dated Feb. 14, 2019", 9 pgs.

"International Application Serial No. PCTIUS2017/045119, International Preliminary Report on Patentability dated Feb. 14, 2019", 8 pgs.

"Japanese Application Serial No. 2018-519441, Notification of Reasons for Refusal dated May 14, 2019", W/ English Translation, 5 pgs.

"Modeling pain with rat dorsal root ganglion neurons on MEAs", Axion Biosystems, [Online] Retrieved from the internet: <https://www.axionbiosystems.com/sites/default/files/resources/modeling_pain_with_rat_dorsaLroot_ganglion_neurons_on_meas.pdf>, (2014), 8 pgs.

Claverol Tinture, E, et al., "Communication; Multielectrode arrays with elastomeric rnicrostructured overlays for extracellular record- (56) References Cited

OTHER PUBLICATIONS ings from patterned neurons; Communication", Journal of Neural Engineering, vol. 2, No. 2, (Jun. 1, 2005), pp. L1-L7.

Walsh, F, et al., "Artificial backbone neuronal network for nano scale sensors", IEEE Conference on Computer Communications Workshop. Shanghai, (2011), pp. 449-454.

"U.S. Appl. No. 14/839,170, Notice of Allowability dated Oct. 17, 2019", 3 pgs.

"U.S. Appl. No. 14/839,170, Notice of Allowance dated Oct. 2, 2019", 8 pgs.

"U.S. Appl. No. 15/199,419, Advisory Action dated Oct. 29, 2019", 5 pgs.

"U.S. Appl. No. 15/199,419, Response filed Nov. 12, 2019 to Advisory Action dated Oct. 29, 2019", 9 pgs.

"U.S. Appl. No. 15/199,419, Response filed Aug. 29, 2019 to Final Office Action dated May 30, 2019", 9 pgs.

"U.S. Appl. No. 15/374,961, Advisory Action dated Sep. 30, 2019", 6 pgs.

"U.S. Appl. No. 15/374,961, Response filed Sep. 12, 2019 to Final Office Action dated Jun. 13, 2019", 7 pgs.

"European Application Serial No. 16829018.7, Response filed Dec. 6, 2019 to Communication Pursuant to Article 94(3) EPC dated May 28, 2019", 9 pgs.

"Japanese Application Serial No. 2018-519441, Response Filed Aug. 14, 2019 to Notification of Reasons for Refusal dated May 14, 2019", w/ English Claims, 9 pgs.

"Japanese Application Serial No. 2018-530058, Notification of Reasons for Refusal dated Jul. 9, 2019", With English Translation, 12 pgs.

"Japanese Applciation Serial No. 2018-530058, Response filed Nov. 13, 2019 to Notification of Resasons for Refusal dated Jul. 9, 2019", w/ English claims, 13 pgs.

"European Application Serial No. 16829018.7, Communication Pursuant to Article 94(3) EPC dated Dec. 20, 2019", 6 pages.

"Japanese Application Serial No. 2018-519441, Notification of Reasons for Refusal dated Jan. 7, 2020", with English translation, 8 pages.

"U.S. Appl. No. 15/789,335, Final Office Action dated Mar. 3, 2020", 29 pages.

"U.S. Appl. No. 15/374,961, Non Final Office Action dated Mar. 17, 2020", 17 pages.

"U.S. Appl. No. 14/839,170, Corrected Notice of Allowability dated Mar. 20, 2020", 5 pages.

Veiseh, M, "Short peptides enhance single cell adhesion and viability on microarrays", Langmuir. 23, (2007), 26 pages.

Yupapin, "Molecular network topology and reliability for multipurpose diagnosis", International Journal of Nanomedicine, (Oct. 18, 2011), pp. 2385-2392.

* cited by examiner

| Day | Task | Media |
|---|---|---|
| | Load Cell Expansion Set | None |
| -1 | Prime Cell Expansion Set | PBS |
| | Coat Bioreactor 12 hours | Matrigel in PBS |
| 0 | IC/EC Washout | IC Inlet: Media<br>EC Inlet: Media |
| | Condition Media | IC Inlet: None<br>EC Inlet: Media |
| | Load Cells with Circulation | IC Inlet: Media<br>EC Inlet: None |
| | Attach Cells 24 hours | IC Inlet: None<br>EC Inlet: Media |
| 1 | Rapid IC Washout | IC Inlet: Media<br>EC Inlet: Media |
| 1-5 | Feed Cells | IC Inlet: Media<br>EC Inlet: None |
| 6 | Add Differentiating Media | IC Inlet: Media<br>EC Inlet: none |
| 6-26 | Feed Cells | IC Inlet: Media<br>EC Inlet: None |
| 26 | Release Adherent Cells | IC / EC washout wit PBS and enzyme load and circulation |
| 26 | Harvest Cells | IC/EC Inlets Harvest media |

METHOD OF MANUFACTURING OR DIFFERENTIATING MAMMALIAN PLURIPOTENT STEM CELLS OR PROGENITOR CELLS USING A HOLLOW FIBER BIOREACTOR

CROSS-REFERENCE TO RELATED APPLICATIONS

This application claims the benefit of the filing date of U.S. application Ser. No. 62/241,977, filed on Oct. 15, 2015, and U.S. application Ser. No. 62/347,208, filed on Jun. 8, 2016, the disclosures of which are incorporated by reference herein.

TECHNICAL FIELD

The present disclosure relates generally to the field of mammalian stem cells, e.g., human-derived induced pluripotent stem cells (iPSc). In one embodiment, the present invention describes how to manufacture iPSc and differentiate iPSc or manufacture neuron progenitor cells on a large scale using a hollow fiber bioreactor. In one embodiment, the present disclosure describes how to manufacture neuron progenitors from iPScs on a large scale using an automated hollow fiber bioreactor.

BACKGROUND

People who regularly culture animal cells become comfortable with standard techniques. However, the typical cycle of seeding cells at very low density in an excess of medium and harvesting just before the point of medium exhaustion is quite an un-physiologic process. Popular culture systems often take cells that originally grew attached to a porous matrix at high densities, with little variability in nutrient and oxygen supply, and adapt them to low-density, styrene-bound or amorphous suspension cultures. Although these methods are well understood and convenient, classical batch-style two-dimensional culture in T-flasks or three-dimensional suspension culture in shake-flasks and bioreactors really is not physiologically relevant.

A remarkable number of alternative culture approaches operating with such unusual mechanisms as rocking bags and depth filters have been introduced over recent years. These are often categorized by characteristics such as suspension/adherent or batch/continuous operation. However, most share two fundamental features: Cells are subjected to wide swings in nutrient, waste, and pH levels from seeding to harvest, and they are generally growing at highly cyclical but relatively low culture densities.

Until recently, the negative consequences of those highly artificial protocols were not well appreciated. But increasing demands of modern drug development, regenerative medicine, and fundamental scientific investigation have inspired the development of alternative approaches. Perfusion culture now exists in a number of (often quite distinct) implementations.

HFPB is a high-density, continuous perfusion culture system. Its hallmark component is a set of thousands of semipermeable hollow fibers in parallel array within a tubular housing or cartridge that is fitted with inlet and outlet ports. The fiber bundles are systematically potted (attached) at each end so that any liquid entering a cartridge will necessarily flow through their interior.

Early commercially available systems from companies as Amicon (now part of Millipore Corporation, www.millipore.com/amicon), Endotronics (now Biovest international, www.biovest.com), and TERUMOBCT www.terumobct.com and offered poor gross filtration rates. Moreover, early units had insufficient nutrient and waste exchange to support the extended culture. Further, large-scale cell culture depends on the mass transfer rates of poorly soluble oxygen, which was the Achilles' heel of early attempts at larger-scale hollow-fiber systems.

SUMMARY OF THE INVENTION

The present disclosure is directed to a method of manufacturing on a large scale in an automated fashion mammalian stem cells and differentiated mammalian stem cells, for instance, mammalian iPSc and differentiated mammalian iPSc cells, or progenitor cells, e.g., neuron progenitor cells, for therapeutic, regenerative and drug screening markets. In particular, in one embodiment, the present disclosure provides seeding, scale up and differentiation of human iPSc that result in functional differentiated cells, such as human cardiomyocytes, by the utilization of a hollow fiber, perfusion bioreactor, which cells can be used for applications including high throughput drug screening. In one embodiment, the present disclosure provides seeding and scale up of human iPSc derived progenitors, such as neuron progenitor cells by the utilization of a hollow fiber perfusion bioreactor. The neuron progenitor cells (NPC) can then be used in applications including high throughput drug screening or differentiated into three dimensional organoids, neurons, or other neuron specific cells type for drug screening, regenerative medicine or therapeutic implants.

The present disclosure is directed to a method of manufacturing on a large scale in an automated fashion mammalian stem cells or progenitor cells, in particular neuron progenitors, for therapeutic, regenerative and drug screening markets. In particular, in one embodiment, the present disclosure provides seeding, scale up of human iPSC derived progenitors, by the utilization of a hollow fiber perfusion bioreactor. The neuron progenitor cells (NPC) can then be used in applications including high throughput drug screening or differentiated into three dimensional organoids, neurons, or other neuron specific cells type for drug screening, regenerative medicine or therapeutic implants.

In one embodiment, the method includes providing a system comprising a hollow fiber bioreactor comprising a plurality of fibers that is part of a sterile closed-loop circuit for media and gas exchange; a gas exchange module; a waste bag; and a cell harvest bag, wherein the fibers are coated with a glycoprotein and a molecule that promotes cell attachment. Stem cells or neuron progenitor cells are introduced to the hollow fibers and the cells are incubated under conditions that allow for cell expansion. In one embodiment, the cells are harvested from the bioreactor. In one embodiment, the cells that are introduced are adherent cells. In one embodiment, the cells that are introduced express one or more of CTIP2, CUX1, MAP2, NEUN, REELIN, SATB2 or TBGR1, any combination thereof or all of CTIP2, CUX1, MAP2, NEUN, REELIN, SATB2 or TBR1. In one embodiment, the cells that are harvested express one or more of CTIP2, CUX1, MAP2, NEUN, REELIN, SATB2 or TBGR1, any combination thereof, or all of CTIP2, CUX1, MAP2, NEUN, REELIN, SATB2 or TBR1. In one embodiment, the glycoprotein is an extracellular matrix glycoprotein. In one embodiment, the glycoprotein enhances attachment and/or spreading of cells. In one embodiment, the molecule that promotes cellular attachment comprises poly-L-ornithine, poly-lysine, Matrigel or a plant derived protein, e.g., Clarisoy™ 170, which contains an isolated soy protein, or Clarisoy™ 180 (Archer Daniel Midland). In one embodiment, fibers comprise polysulfone or cellulose derivatives, e.g., polyvinylidene fluoride or polyolefins. In one embodiment, the conditions include control of gas exchange, control of temperature, control of metabolite concentration, control of growth factor concentration, or time, or any combination thereof. In one embodiment, the conditions include cell culture media comprising, FGF-2, BDNF and/or GDNF.

DETAILED DESCRIPTION

Figure 1:
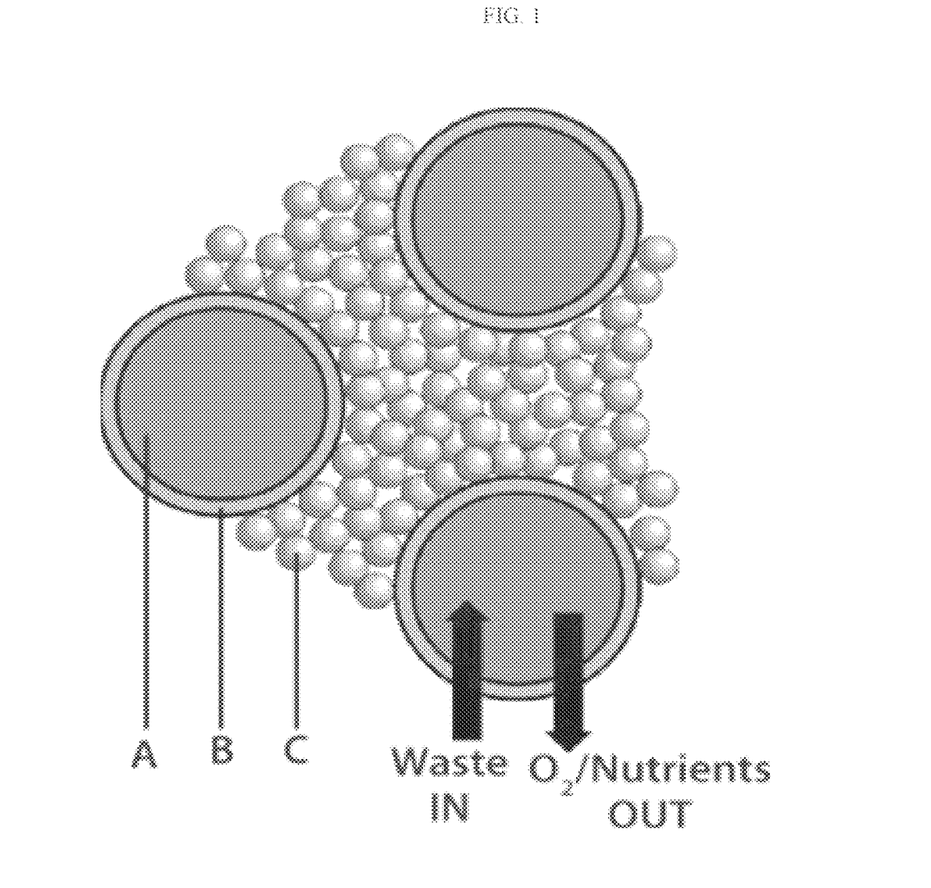
FIG. 1 shows a cross section of a typical hollow fiber reactor.

Hollow-fiber-based technologies in general are used in many applications, from tangential-flow filtration to prokaryotic biofilms in wastewater treatment. Here, hollow-fiber perfusion bioreactor (HFPB) technology is employed in the culture of mammalian cells. Mammalian cells can be generally seeded within a cartridge intra capillary space (IC), labeled A in FIG. 1, and outside the hollow fibers in what is referred to as the extra capillary space (EC), labeled B in FIG. 1. The cells are labeled C in FIG. 1 and reside in the EC space. The IC and EC are thus separated by a fiber wall which acts as a membrane. Culture medium is pumped through the lumen of the hollow fibers, allowing nutrients and metabolic products to diffuse both ways across the fiber walls. Having passed through the cartridge, medium can be either oxygenated and returned to it or collected while fresh medium is introduced.

In most culture systems, cells are seeded in a medium containing a great excess of nutrients and no metabolic products. They progress for a matter of days in an environment of declining nutrients and increasing products, only to be suddenly exposed to the original media composition again (when the culture is split into fresh media) or to a slightly different variation of the original formulation (during serial adaptation of a culture to a new medium). Recent advances in metabolic flux analysis support the significance of such exposure to a variable and even discontinuous cycle of nutrient and metabolic products. However, the relative constancy of the culture matrix and ambient chemical environment in an HFPB system provides a more consistent and physiologic culture environment. Because freshly oxygenated medium is continually exchanged through an immobilized culture, cells exist in an environment of relatively constant metabolite and growth factor concentration. This benefits a number of applications. For example, some primary and specialized cell lines tend to regulate critical pathways, differentiate, or "shock" in response to significant or sudden changes in their medium.

The HFPB culture chamber environment is continuously controllable in real time. Because HFPB systems possess such an efficient medium-exchange mechanism, it is easy to alter the input medium composition (and therefore the ambient cellular environment) whenever desired. This differs from fed-batch cultures, which allow only the addition of a bolus of nutrients or reagents on top of existing media components. Furthermore, high-density culture in the controlled hydrodynamic conditions of an HFPB can provide a microenvironment of directional flow, establishing a gentle interstitial gradient within the cell mass for autocrine stimulation, cell alignment, and desirable cell-cell or cell-surface interactions.

Because an HFPB cell culture (on the EC side of the fibers) exists at concentrations ≥100× that of standard suspension cultures, less serum is needed and product may be harvested at many times the concentration of that from most other systems. Other benefits include facilitation of adapting cultures to serum-free media and better support for conditioned media and autocrine-dependent cultures. The initial volume of a circulating loop can be very low when a culture is seeded, then raised as the cell number increases, thereby maintaining a more constant cell/medium ratio.

Cells in HFPB culture are separated from the bulk of their medium by a membrane (e.g., fiber wall) of definable composition and porosity. The cells essentially experience two different volumes: That seen for low-molecular-weight components such as glucose and lactate is relatively large, whereas the volume seen for larger components and some stimulatory cytokines is ≥100× smaller. Because both the culture (EC) and perfused medium (fiber lumen; IC) sides of the system are accessible to sampling and feeding, it is common to maintain and monitor particular components within each distinct space. This provides for many valuable functions in operation.

For example, the volume of the cell-containing compartment can be quite small, so products can be harvested at 100× or higher concentration than from suspension culture. By matching a reactor's fiber porosity to cell characteristics, products may be accumulated, maintained, and measured on either side of the system. In one application, macromolecular culture factors can be introduced or allowed to accumulate within the EC side.

Combining such features as an unlimited nutrient supply and the ability to "debulk" a culture through the cartridge ports allows an HFPB system to be maintained at relative equilibrium for several months or longer. Continuous production over long periods provides several benefits over batch cultures: consistency in culture condition, dramatically increased production per unit footprint and culture volume, continuous or daily product harvest that allows timely stabilizing treatment or storage conditions, and the option of continually removing products from a culture that might be toxic or inhibitory to cells.

The large number of ex vivo expanded cells that are required in many high throughput drug screening, roughly 2 million per 384 plate, and clinical cell therapy protocols (>200 million per patient) make standard culture conditions problematic and expensive, resulting in the need for extensive personnel and facilities resources, and the potential for contamination. To meet such clinical demand, a robust automated and closed cell expansion method is optimal. The HFPB system useful in the present methods is a functionally closed, automated hollow fiber bioreactor system designed to reproducibly grow both adherent and suspension cells in either GMP or research laboratory environments. The system has been used for the ex vivo expansion of clinical-scale quantities of human mesenchymal stem cells (MSC). MSCs from precultured cells were expanded in the system with media consisting of α-MEM, 10 percent FBS, 1× Gluta-MAX and no additional antibiotics/antimycotics or supplementary factors. Glucose and lactate levels in the media were monitored to maintain optimal culture conditions. The HFPB system-expanded MSCs met all typical MSC characteristics for phenotype and differentiation. Cell numbers suitable for therapeutic dosages of MSC were generated in five days from initial cell loads of about 15 to about 20 million cells.

Figure 2:
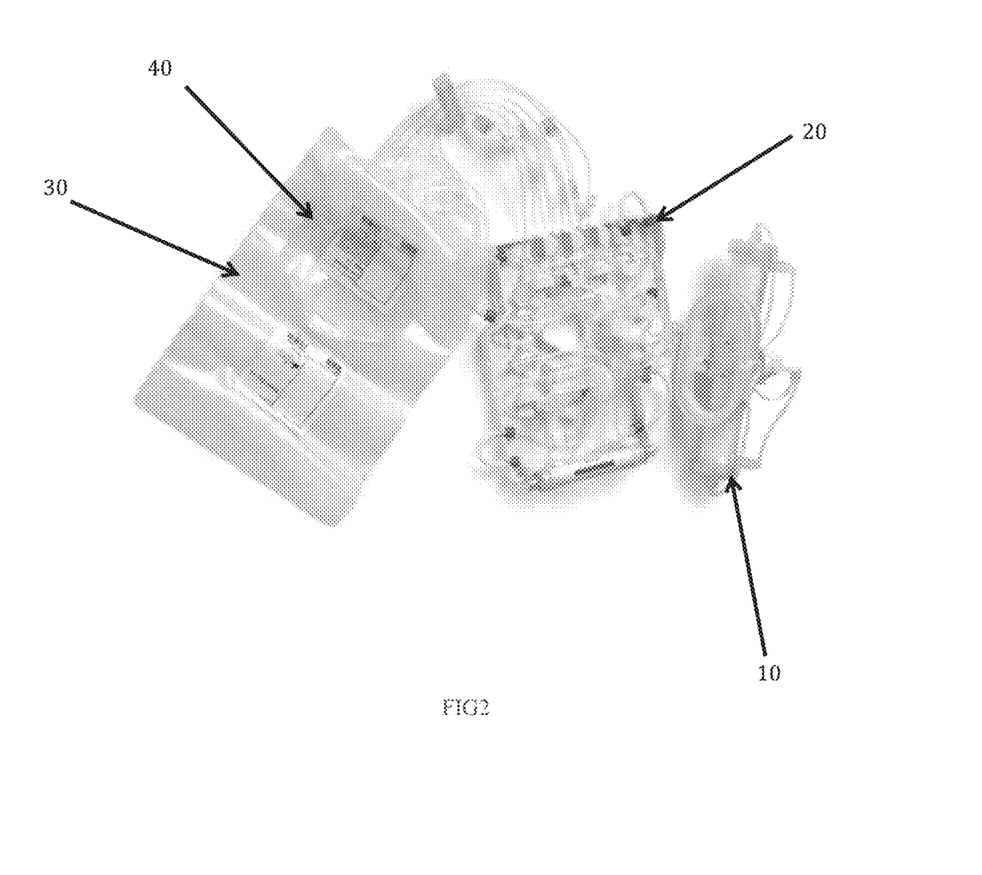
FIG. 2 shows an image of a typical hollow fiber reactor fluid loop used in a hollow fiber perfusion bioreactor (HFPB).

The HFPB system is a functionally closed, automated hollow fiber bioreactor system designed to grow both adherent and suspension cells. As shown in FIG. 2, the bioreactor culture system is comprised of a synthetic hollow fiber bioreactor 10 that is part of a sterile closed-loop circuit for media and gas exchange, a gas exchange module 20, a pre-attached waste bag 30 and a pre-attached cell harvest bag 40.

A wide range of materials, such as polysulfone and cellulose derivatives, may be used for the hollow fibers. Molecular weight cutoffs begin at 5 kDa and go up to virtually any desired upper limit. The fiber materials can vary in such properties as percent porosity, molecular weight cut-off, and hydrophilicity, and they can be further modified during either manufacturing or their actual application to introduce defined functionalities onto their surfaces. Characteristics of an HFPB system are: Extremely high binding culture surface to volume ratios, immobilization of cells at a very high (biomimetic) density on a porous matrix supporting prolonged culture selectable porosity of the fibers for such purposes as concentration of secreted products or delivered media, differentiation factors, and enzymes of interest.

In one embodiment, the bioreactor and fluid circuit are a single-use disposable set that is mounted onto the Quantum system unit that can be purchased from TERUMOBCT Corporation in Lakewood, Colo. In one embodiment, the bioreactor may be comprised of about 11,500 hollow fibers with a total intracapillary (IC) surface area of 2.1 m². Typical culture manipulations (e.g., cell seeding, media exchanges, differentiation factors, trypsinization, cell harvest, etc.) are managed by the computer-controlled system using pumps and automated valves, which direct fluid through the disposable set and exchanges gas with the media. The functionally closed nature of the disposable set is maintained through the sterile docking of bags used for all fluids; these bag connections/disconnections all utilize sterile connection technology. In one embodiment, gas control in the system is managed using a hollow fiber oxygenator (gas transfer module 20. FIG. 2). In one embodiment, gas is supplied from a user-provided premixed gas tank. By choosing a tank with the desired gas mixture, the user can expand cells at their optimal gas concentration. In one embodiment, the IC membrane of the bioreactor may be coated with an adhesion promoter such as fibronectin, matrigel, gelatin or combinations of the aforementioned promoters to allow the attachment of adherent cell populations, such as iPSc, neuron progenitor cells or cardiomyocytes.

In one embodiment, after loading a new cell expansion set using the Load Cell Expansion Set Task (every run/passage requires the use of a new disposable set to assure process sterility), the disposable set may be primed with PBS in the 4 L Media Bag that has been connected to the Cell Inlet line of the disposable set using a Terumo® TSCD or TSCDII sterile connection device. In one embodiment, the Media Bag Accessory is filled with fluid from reagent bottles under a biosafety cabinet utilizing a tubing pump (Cole-Parmer Masterflex® L/S Tubing Pump with the Easy-Load II pump header) to pump the fluid into the Media Bag Accessory; all sealing of disposable tubing lines is done with an RF Sealer (Sebra Omni™ 2600 Sealer). In one embodiment, once the disposable set has been primed, the bioreactor is coated overnight with 10 mg of matrigel to promote cell adhesion using the Coat Bioreactor Task. In one embodiment, the matrigel is prepared by solubilizing 10 mg of matrigel in 20 mL of sterile $H_2O$ for 30 minutes, bringing the solution volume to 100 mL with 80 mL of PBS, transferring the matrigel solution to a Cell Inlet Bag in a biosafety cabinet. In one embodiment, after the overnight bioreactor coating, any excess matrigel is washed from the bioreactor set and the cell culture media is introduced into the set utilizing the IC/EC Washout Task allowing the exchange of PBS solution with Media, which has been filled into a 4 L Media Bag accessory and sterile connected to the IC Inlet Line. To assure that the newly introduced Media is properly oxygenated, in one embodiment, the Condition Media Task is run for a minimum of 10 minutes. In one embodiment, the gas mixture used is 20 percent $O_2$, 5 percent $CO_2$ and the balance $N_2$. At this point the disposable set is ready to be used for cell loading and expansion.

In one embodiment, fifteen to twenty million pre-cultured iPSc are transferred into the cell inlet bag of the HFPB and the volume is brought up to 100 mL with the growth media of interest. In one embodiment, the bag is then connected to the inlet line of the HFPB and the cells loaded onto the IC side of the bioreactor utilizing the Load Cells with circulation program. This step is designed to allow uniform distribution of the cells throughout the IC side of the bioreactor. Once this task is complete, in one embodiment, the system is put in the Attach cells task mode, which allows the cells to adhere to the IC membrane surface. In one embodiment, the IC media flow rate is zero to allow the cell attachment, while the EC flow rate may be approximately 30 mL/min to maintain oxygenation in the bioreactor. In one embodiment, the cells are allowed to attach for 24 to 48 hours optionally followed by a rapid IC washout to remove any nonadherent cells.

In one embodiment, cells are grown for four days utilizing the Feed Cells Task with fresh media added to the IC side of the bioreactor and the IC inlet rate adjusted as required by the rate of glucose consumption and lactate generation in the system which is monitored from a sample port twice daily. Depending on the teed rates, in one embodiment, a standard 5-day expansion typically consumes about 8 liters of media when loaded with 15-20 million cells. The IC waste valve is open for the duration of the expansion phase to allow waste media to collect in the waste bag to prevent protein accumulation in the IC loop.

In one embodiment, after 5-7 days the expansion is complete and now the cells are exposed to a number of factors that induce differentiation into cardiomyocytes in the present invention. In one embodiment, at this point of the expansion there are 500 million to 1 billion cells in the MPH and the doses and correct concentrations of the differentiation factors are added. An example of such media comprises a mixture of RPMI, DMEM and M199 media, a GSK3-beta inhibitor, a Wnt inhibitor, insulin, human serum albumin, and ascorbic acid. The cells may differentiate over a period of for example, 20 days and during that time, n one embodiment, the growth media is changed every other day to remove waste and keep the cells viable until harvest.

In one embodiment, on day approximately 26 expanded and differentiated human iPSc cardiomyocytes are released from the IC membrane of the bioreactor using a 0.25 percent trypsin-EDTA or equivalent enzyme package as the adherent cell release agent. Other enzymes can be used depending on the type of hollow fibers used in the bioreactor such as cellulase and collagenase. In one embodiment, the Release Adherent Cells Task is used to flush media from the system with PBS, then to fill the bioreactor with the enzyme solution that is circulated in the bioreactor from 4 to 10 minutes. Once this task is complete, released cells are harvested utilizing the Harvest task with the proper harvest media in the Harvest bag attached to the IC inlet line. Once the harvest is complete the harvest bag is sealed and detached from the reactor. The cells can be subsequently removed from the bag for cell counting, viability analysis, phenotyping, morphology, and differentiation assays.

In one embodiment, after loading a new cell expansion set using the Load Cell Expansion Set Task (every run/passage requires the use of a new disposable set to assure process sterility), the disposable set may be primed with PBS in the 4 L Media Bag that has been connected to the Cell Inlet line of the disposable set using a Terumo® TSCD or TSCDII sterile connection device. In one embodiment, the Media Bag Accessory is filled with fluid from reagent bottles under a biosafety cabinet utilizing a tubing pump (Cole-Parmer Masterflex® L/S Tubing Pump with the Easy-Load II pump header) to pump the fluid into the Media Bag Accessory; all sealing of disposable tubing lines is done with an RF Sealer (Sebra Omni™ 2600 Sealer). In one embodiment, once the disposable set has been primed, the bioreactor is coated overnight with 10 mg of matrigel to promote cell adhesion using the Coat Bioreactor Task. In one embodiment, the matrigel is prepared by solubilizing 10 mg of matrigel in 2.0 mL of sterile $H_2O$ for 30 minutes, bringing the solution volume to 100 mL with 80 mL of PBS, transferring the matrigel solution to a Cell Inlet Bag in a biosafety cabinet. In one embodiment, after the overnight bioreactor coating, any excess matrigel is washed from the bioreactor set and the cell culture media is introduced into the set utilizing the IC/EC Washout Task allowing the exchange of PBS solution with Media, which has been filled into a 4 L Media Bag accessory and sterile connected to the IC Inlet Line. To assure that the newly introduced Media is properly oxygenated, in one embodiment, the Condition Media Task is run for a minimum of 10 minutes. In one embodiment, the gas mixture used is 20 percent $O_2$, 5 percent $CO_2$ and the balance $N_2$. At this point the disposable set is ready to be used for cell loading and expansion.

In one embodiment, eighty to one hundred million NPCs are transferred into the cell inlet bag of the HFPB and the volume is brought up to 100 mL with the growth media of interest. In one embodiment, the bag is then connected to the inlet line of the HFPB and the cells loaded onto the IC side of the bioreactor utilizing the Load Cells with circulation program. This step is designed to allow uniform distribution of the cells throughout the IC side of the bioreactor. Once this task is complete, in one embodiment, the system is put in the Attach cells task mode, which allows the cells to adhere to the coated IC membrane surface. In one embodiment, the IC media flow rate is zero to allow the cell attachment, while the EC flow rate may be approximately 30 mL/min to maintain oxygenation in the bioreactor. In one embodiment, the cells are allowed to attach for 24 to 48 hours optionally followed by a rapid IC washout to remove any nonadherent cells.

In one embodiment, cells are grown for at least three to five days utilizing the Feed Cells Task with fresh media added to the IC side of the bioreactor and the IC inlet rate adjusted as required by the rate of glucose consumption and lactate generation in the system which is monitored from a sample port twice daily. The IC waste valve is open for the duration of the expansion phase to allow waste media to collect in the waste bag to prevent protein accumulation in the IC loop.

In one embodiment, after 5-7 days the expansion is complete. In one embodiment, at this point of the expansion there are 500 million to 2 billion cells in the HFPB. In one embodiment, cells are released from the IC membrane of the bioreactor using a 0.25 percent trypsin-EDTA or equivalent enzyme package as the adherent cell release agent. Other enzymes can be used depending on the type of hollow fibers used in the bioreactor such as cellulase and collagenase. In one embodiment, the Release Adherent Cells Task is used to flush media from the system with PBS, then to fill the bioreactor with the enzyme solution that is circulated in the bioreactor from 4 to 10 minutes. Once this task is complete, released cells are harvested utilizing the Harvest task with the proper harvest media in the Harvest bag attached to the IC inlet line. Once the harvest is complete the harvest bag is sealed and detached from the reactor. The cells can be subsequently removed from the bag for cell counting, viability analysis, phenotyping, morphology, and differentiation assays.

In one embodiment, eighty to one hundred million NPCs are transferred into the cell inlet bag of the HFPB and the volume is brought up to 100 mL with the growth media of interest. In one embodiment, the bag is then connected to the inlet line of the HFPB and the cells loaded onto the IC side of the bioreactor utilizing the Load Cells with circulation program. This step is designed to allow uniform distribution of the cells throughout the IC side of the bioreactor. Once this task is complete, in one embodiment, the system is put in the Attach cells task mode, which allows the cells to adhere to the coated IC membrane surface. In one embodiment, the IC media flow rate is zero to allow the cell attachment, while the EC flow rate may be approximately 30 mL/min to maintain oxygenation in the bioreactor. In one embodiment, the cells are allowed to attach for 24 to 48 hours optionally followed by a rapid IC washout to remove any nonadherent cells.

In one embodiment, cells are grown for at least three to five days utilizing the Feed Cells Task with fresh media added to the IC side of the bioreactor and the IC inlet rate adjusted as required by the rate of glucose consumption and lactate generation in the system which is monitored from a sample port twice daily. The IC waste valve is open for the duration of the expansion phase to allow waste media to collect in the waste bag to prevent protein accumulation in the IC loop.

In one embodiment, after 5-7 days the expansion is complete. In one embodiment, at this point of the expansion there are 500 million to 2 billion cells in the HFPB. In one embodiment, cells are released from the IC membrane of the bioreactor using a 0.25 percent trypsin-EDTA or equivalent enzyme package as the adherent cell release agent. Other enzymes can be used depending on the type of hollow fibers used in the bioreactor such as cellulase and collagenase. In one embodiment, the Release Adherent Cells Task is used to flush media from the system with PBS, then to fill the bioreactor with the enzyme solution that is circulated in the bioreactor from 4 to 10 minutes. Once this task is complete, released cells are harvested utilizing the Harvest task with the proper harvest media in the Harvest bag attached to the IC inlet line. Once the harvest is complete the harvest bag is sealed and detached from the reactor. The cells can be subsequently removed from the bag for cell counting, viability analysis, phenotyping, morphology, and differentiation assays.

Figure 3:
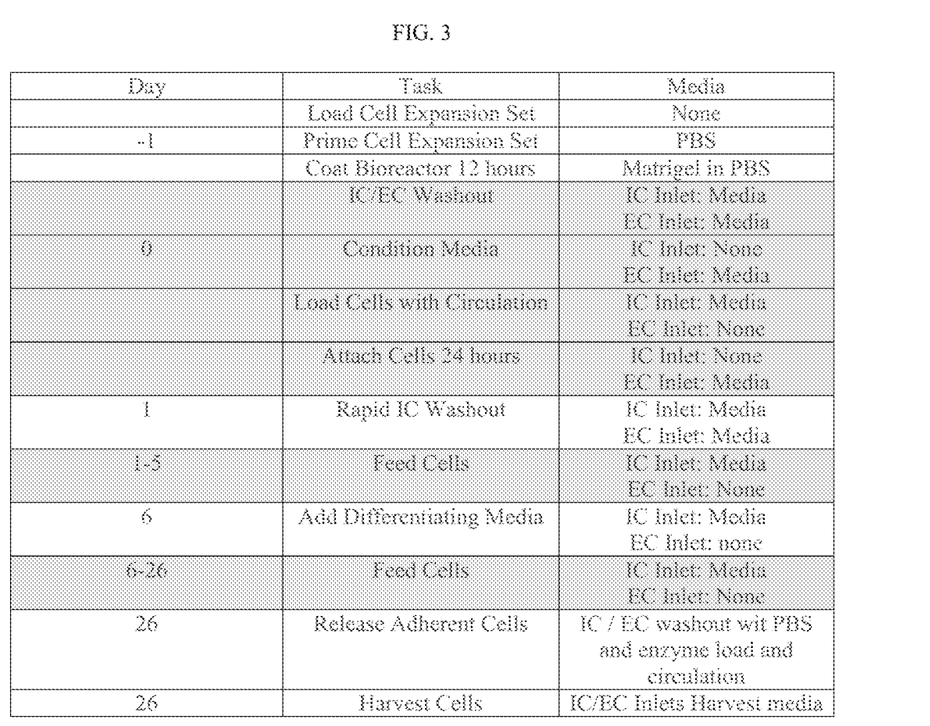
FIG. 3 shows a flow chart of an exemplary manufacturing process, e.g., for iPSc.

A flow diagram table describing the process is shown in FIG. 3.

The invention will be described by the following non-limiting example.

Example

A. Neural Progenitor Cells Materials/Equipment
a. Consumables
   i. Quantum Expansion Set (1×)
   ii. 4 L Media Bag (9×)
   iii. Cell Inlet Bag (5×)
   iv. Waste Bag (5×)
   v. Gas Supply (5% $CO_2$, 20% $O_2$, Balance with $N_2$)
   vi. Glucose strips
   vii. Lactate strips
b. Media/Reagents
   i. DMEM/F12 (Cat #: 11330-032, Corning)
   ii. PBS without calcium and magnesium
   iii. Poly-L-Ornithine (PLO, Cat #: P3655, Sigma)
   iv. Laminin (Cat #: 23017-015, Invitrogen)
   v. Accutase Cell Dissociation Reagent (Cat #: A11105-01, Thermo)
   vi. B27, N2 Supplements
   vii. Fibroblast Growth Factor-2 (FGF-2)
   viii. BDNF (Brain-derived neurotropic factor)
   ix. GDNF (Glial cell-derived neurotropic factor)
B. Procedures (Expansion)
a. Load Cell Expansion set
b. Prime the expansion set with 2 Ls of DMEM/F12 in a "Cell" Line
c. Prepare extracellular matrix for neural progenitor cells with PLO/Laminin.
   i. PLO preparation: Dissolve the PLO powder in cell culture water to make a stock solution of 10 mg/mL and aliquot 1 mL portions. Dilute the stock solution of 10 mg/mL in cell culture water to yield 10 µg/mL (1:1000).
      1. Put 100 mL of cell culture water in an empty 125 mL bottle, and add 100 µL of the stock solution (10 mg/mL) of PLO. Put the 100 mL solution in the reagent bag.
   ii. Laminin preparation: Dilute Laminin in PBS—(Sigma-Aldrich PS244) to yield 5 µg/mL (1:200)
      1. Put 100 mL of PBS—in an empty 125 mL bottle, and add 500 uL of the stock solution of Laminin to yield 5 µg/mL (1:200). Put the 100 mL solution in the reagent bag and store the reagent bag in a 4'C refrigerator.
   iii. Prepare 4 L of cell culture water in a media bag.
d. Coating Bioreactor
   i. Connect the prepared PLO reagent bag to the "reagent" line. Coat the bioreactor overnight at 37'C.
   ii. Next day, wash the bioreactor three times with 1.4 L of cell culture water prepared in step B,iii by performing IC/EC (intracapillary/extracapillary space) washouts.
      1. Each washout removes about 90% of IC/EC volume.
   iii. Disconnect the PLO reagent bag, and connect the Laminin filled reagent bag to the "reagent" line, and coat the bioreactor for at least 2 hours.
e. Make 2 L of NBF media and introduce to a media bag.
i. 0.5× N-2 supplement, 0.5× B-27 supplement and 1× Pencillin-Streptomycin in DMEM/F12 50/50 mix media.
f. Perform IC/EC washout with NBF and condition media until cells are ready to load.
g. Load about 80 million NPCs by dissociating about 10×10 cm dishes of NPCs.
h. Attach the cells
i. Feed the cells with appropriate volume of media and flow rate.
   i. After 24 hours of attachment iPSCs which is now day 1, start feeding the cells at 0.1 mL/minute. Measure the glucose/lactate and record every day until the expansion run is finished.
      1. On Day 2, make 300 ml of NBF and load it in a media bag. Feed the cells at 0.2 mL/minute.
      2. On Day 3, make 600 ml of NBF and load it in a media bag. Feed the cells at 0.4 mL/minute.
      3. On Day 4, make 1200 ml of NBF and load it in a media bag. Feed the cells at 0.8 mL/minute.
      4. On Day 5, make 2400 ml of NBF and load it in a media bag. Feed the cells at 1.6 mL/minute.
      5. **Media preparation for each day might be different and adjustable, but the final harvested number of cells would be about 1.3 billion cells, with possibly about 1.0 billion live cells.
j. Make a 2 L media bag with PBS—and a 100 ml reagent bag with Accutase (Keep the reagent bag in a 37'C water bath).
k. Start harvesting the expanded NPCs by performing IC/EC washout in the bioreactor once with the 2 L PBS—, and then dissociating with pre-heated 100 ml Accutase for approximately 5 minutes.
l. All the harvested cells are in the "harvest" bag. Transfer the bag into a biosafety cabinet hood. Cut the harvest bag and put the cells in 50 mL conical tubes. Centrifuge at 200×g for 5 minutes and re-suspend the pellet with 100 mL of fresh NBF.

Following the aforementioned protocol resulted in the following neuroprogenitor cell expansion results after 7 days.
Average cell counts
1. Total cells: 841 M (loaded app. 100 M)
2. Live cells: 644 M
3. Viability: 76%

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed:
1. A large-scale method to expand mammalian neuron progenitor cells, comprising:
providing a system comprising a hollow fiber bioreactor comprising a plurality of hollow fibers that is part of a sterile closed-loop circuit for media and gas exchange; a gas exchange module; a waste bag; and a cell harvest bag, wherein the hollow fibers are coated with laminin and poly-L ornithine and optionally other molecules that promote cell attachment, wherein the molecular weight cutoff of the hollow fibers is about 5 kDa;
introducing the neuron progenitor cells to the hollow fibers;
incubating the neuron progenitor cells in the hollow fibers under culture conditions that allow for neuron progenitor cell expansion of at least 5 fold in about 5 days, wherein the culture conditions include a serum-free medium comprising brain-derived neurotrophic factor

(BDNF), glial cell-derived neurotrophic factor (GDNF) and fibroblast growth factor-2 (FGF-2); and harvesting the expanded neuron progenitor cells from the bioreactor.

2. The method of claim 1 wherein the hollow fibers comprise polysulfone or cellulose derivatives.

3. The method of claim 1 wherein the other molecules enhance spreading of the neuron progenitor cells in the hollow fibers.

4. The method of claim 1 other molecules comprise fibronectin, vitronectin, or a combination thereof.

5. The method of claim 1 wherein the other molecules comprise poly-lysine, Matrigel® or a plant derived protein.

6. The method of claim 1 wherein the neuron progenitor cells are obtained from induced pluripotent stem cells (iPSc).

7. The method of claim 1 wherein the culture conditions include control of gas exchange, control of temperature, control of metabolite concentration, control of growth factor concentrations, or time, or any combination thereof.

8. The method of claim 1 wherein introducing the neuron progenitor cells includes allowing said cells to adhere to the hollow fibers.

9. The method of claim 1 wherein the expanded neuron progenitor cells are harvested after at least 7 days of expansion.

10. The method of claim 1 wherein the expanded neuron progenitor cells are harvested after at least 5 days of expansion.

* * * * *